United States Patent [19]

Ono et al.

[11] Patent Number: 5,080,908
[45] Date of Patent: Jan. 14, 1992

[54] VITAMIN $B_{12}$ COMPOSITION

[75] Inventors: Yasuo Ono, Osaka; Kunihiko Sumimura, Tokyo; Junzou Yamashita, Toyonaka, all of Japan

[73] Assignee: Takeda Chemical Industries, Ltd., Osaka, Japan

[21] Appl. No.: 574,194

[22] Filed: Aug. 28, 1990

[30] Foreign Application Priority Data

Aug. 31, 1989 [JP] Japan .................... 1-226513

[51] Int. Cl.⁵ .................... A61K 9/16; A61K 9/50; A61K 31/70
[52] U.S. Cl. .................... 424/499; 514/52; 514/951
[58] Field of Search .................... 514/52, 951, 778; 424/499

[56] References Cited

U.S. PATENT DOCUMENTS

| | | | |
|---|---|---|---|
| 2,830,933 | 4/1958 | Bouchard et al. | 514/52 |
| 4,486,435 | 12/1984 | Schmidt et al. | 514/52 |

FOREIGN PATENT DOCUMENTS

| | | |
|---|---|---|
| 1064790 | 9/1959 | Fed. Rep. of Germany . |
| 1617626 | 3/1971 | Fed. Rep. of Germany . |
| 49-16930 | 4/1974 | Japan . |
| 59-152327 | 8/1984 | Japan . |
| 1-203329 | 8/1989 | Japan . |
| 1420833 | 1/1976 | United Kingdom . |

OTHER PUBLICATIONS

*Handbook of Pharmaceutical Excipients* (1986), pp. 93-94.

*Primary Examiner*—Frederick E. Waddell
*Assistant Examiner*—Raymond J. Henley, II
*Attorney, Agent, or Firm*—Wenderoth, Lind & Ponack

[57] ABSTRACT

A vitamin $B_{12}$ composition wherein vitamin $B_{12}$ exists as dispersed in a mixture of starch and dextrin can keep vitamin $B_{12}$ stable for a long time and can be easily manufactured by the ordinary convenient method without employing any special equipment.

2 Claims, No Drawings

VITAMIN $B_{12}$ COMPOSITION

The present invention relates to a stable and inexpensive vitamin $B_{12}$-containing composition which can be provided as powders, fine granules, granules, capsules, pills or tablets in the areas of food, medicine and animal feed.

The quantity of vitamin $B_{12}$ group compounds used in pharmaceutical and other solid preparations is generally very small. For example, the Standard for Approval to Manufacture (Import) Pharmaceutical Products Containing Vitamins as Active Ingredients (Feb. 1, 1988) of Japan specifies that the daily dose or formulation amount of cyanocobalamin and hydroxocobalamin is 1 to 1,500 μg.

Therefore, vitamin $B_{12}$ compounds are generally used adsorbed on an inert excipient (such as lactose, starch, etc.) as diluted powders (for example, a 100-fold powder for 1% concentration) for insuring the uniformity of content.

The commercial preparations containing such inert excipients, available today, include a mannitol-adsorbed powder (Merck, vitamin $B_{12}$-mannit-verreibung, 0.1%), a lactose-adsorbed powder (Merck, vitamin $B_{12}$-lactose-verreibung, 0.1%) and a dibasic calcium phosphate-adsorbed powder (H. Reisman Corporation, cyanocobalamin USP 0.1% trituration W/dibasic calcium phosphate), to name but a few.

It is also known that vitamin $B_{12}$ compounds generally become unstable upon dilution and are poorly compatible with other drugs and additives. According to Campbell, for instance, the stability of vitamin $B_{12}$ is adversely affected in the presence of ascorbic acid, nicotinamide, thiamin, talc, sucrose, metal ions and so on (Campbell, J. A., J. Pharm. Sci. 44, 263, 1955).

Therefore, when vitamin $B_{12}$ compounds are to be incorporated in solid preparations, it is common practice to isolate them from other agents or insure the uniformity of content either by using a stable adsorbed powder such as those mentioned above or by preparing a composition containing vitamin $B_{12}$ and other compatible agents in the first place and subsequently combining it with another agent or composition of agents that may affect the stability of vitamin $B_{12}$ compounds. For the preparation of tablets, resort is had to various contrivances such as isolation by way of press-coated tablet or multilayer tablet or in the case of manufacture of coated tablets, addition of vitamin $B_{12}$ to the coating layer.

Furthermore, as a preparation designed to enhance the stability of vitamin $B_{12}$ compounds adsorbed on the carrier, an adsorbed $B_{12}$ powder (Hoffman-LaRoche Inc., vitamin $B_{12}$ 0.1% SD), which comprises fine particulate vitamin $B_{12}$ coated with a modified food starch derivative, is available on the market. Generally speaking, this adsorbed powder is manufactured by spray-drying an aqueous suspension or solution of vitamin $B_{12}$ compounds together with an adsorbent (Japanese Kokai Patent Application No. 49-108224).

As a still another approach to stabilization, Gupta et al. proposed microencapsulation by an emulsion technique using shellac and macrogol 6000 [R. G. Gupta and B. C. Rao, Drug Devel. and Ind. Pharm., 11(1), 41-53 (1985)].

A vitamin $B_{12}$ preparation using alpha-starch as the adsorbent carrier has also been proposed (Japanese Kokai Patent Application No. 63-28245).

Among the other vitamin $B_{12}$ preparations known today are a preparation using a cation exchange resin as the adsorbent (U.S. Pat. No. 2,830,933) and a dispersion of vitamin $B_{12}$ in a gelatin matrix.

As mentioned above, powders using mannitol, lactose or dibasic calcium phosphate are unsatisfactory in formulation stability and require many complicated pharmaceutical procedures, inter alia, for isolated preparation of mixing batches and special tableting technology.

Furthermore, the spray-dried preparation based on modified food starch, the preparation containing alpha-starch, and the preparation based on a gelatin matrix also have various drawbacks such as complicated manufacturing processes, high general material costs, large-scale equipment required and high adsorbent costs, all of which contribute to high product costs. Therefore, the development of a vitamin $B_{12}$ composition meeting the following requirements has been keenly demanded.
1) Can be manufactured by simplified production technology and equipment
2) Be stable in formulation with other agents
3) Can be directly molded into tablets even in formulation with other agents.
4) Be inexpensive To overcome the aforementioned disadvantages, the inventors of the present invention prepared a vitamin $B_{12}$ composition using an adsorbent carrier consisting of starch and dextrin, which is an inexpensive diluent, and found that this composition is remarkably improved in formulation stability which had not been available with starch alone. The present invention has been developed on the basis of the above finding.

The present invention is, therefore, directed to a vitamin $B_{12}$ composition in which vitamin $B_{12}$ exists as dispersed in a mixture of starch and dextrin.

As species of vitamin $B_{12}$, there may be mentioned cyanocobalamin, hydroxocobalamin, hydroxocobalamin hydrochloride, hydroxocobalamin acetate, coenzyme type vitamin $B_{12}$ and other corrinoids.

With regard to the starch, granular starch can be used as such. To be specific, corn starch, potato starch, wheat starch, rice starch, tapioca starch, etc. can be mentioned.

The dextrin mentioned above is available on hydrolysis of starch and various types of dextrin can be used. To be specific, erythrodextrin, acrodextrin, maltodextrin, etc. can be mentioned. Generally, dextrins showing colors in the range of colorless to brown to red in the test for iodine as directed in the Pharmacopoeia of Japan or those with molecular weights not exceeding about 10,000 are employed. Preferably, the commercial products listed on the Pharmacopoeia of Japan can be employed.

In the manufacture of a composition of the invention, dextrin and starch are mixed together in the first place. The mixing ratio is 5 to 30 weight percent of dextrin on a total amount of vitamin $B_{12}$, dextrin and starch. The preferred proportion of dextrin is 10 to 20 weight percent on the same basis.

When the proportion of dextrin is less than 5 weight percent, vitamin $B_{12}$ may not be sufficiently dispersed. On the other hand, when the proportion exceeds 30 weight percent, the particles of the composition become too hard to assure the proper disintegration of tablets prepared from the composition.

The mixing can be achieved by the usual method for blending solid materials insofar as a uniform mixture can be obtained.

Then, the vitamin $B_{12}$ compound or compounds are dissolved in water or in an organic solvent diluted with water.

This solution is then added to the starch-dextrin mixture prepared as above and the composition is mixed well to give a uniform dispersion of vitamin $B_{12}$, which is then dried. This mixing can be carried out by the conventional method using a kneader or a high speed mixer.

An alternative technique that can be used comprises fluidizing the above mixture in a fluidized-bed equipment and spray-drying the above solution of vitamin $B_{12}$.

The proportion of vitamin $B_{12}$ is 0.05 to 1.0 weight percent on a total amount of vitamin $B_{12}$, starch and dextrin. The preferred proportion is in the range of 0.1 to 1.0 weight percent. In dissolving vitamin $B_{12}$ in water, it is recommended that the concentration be controlled to less than the saturated concentration. Thus, the aqueous solution is prepared in a concentration not higher than 8% (w/v) and preferably in the range of 0.4 to 7% (w/v).

When the aqueous solvent is used as aforesaid, an organic solvent may be added to water. The use of ethanol, in particular, facilitates dispersion of vitamin $B_{12}$ compounds.

When the fluidized-bed granulation technique is used, a dilute aqueous solution is generally employed. The volume of the solution may be chosen according to the equipment employed.

The resulting granules can be subjected to size selection or comminuted to give a desired preparation.

For formulation with other agents, a powder with a particle size not exceeding 100 μm is preferred.

The vitamin $B_{12}$ composition of the present invention is stable as it is and because of the use of a mixture of starch and dextrin, it can be easily manufactured by the ordinary convenient method without employing any special equipment.

When the composition of the invention is used, vitamin $B_{12}$ compounds remain stable in the formulations without any appreciable aging such as content loss.

Furthermore, since the vitamin $B_{12}$ composition of the invention contains dextrin, it can be simply admixed with commercial direct compressible granules of vitamin. $B_1$, vitamin $B_6$, vitamin C, etc. and the mixture can be subjected to direct compression. This is an effect which cannot be achieved with the use of starch alone.

Moreover, since the composition of the invention can be manufactured using commercial grades of starch and dextrin, the starting materials themselves need not be modified at all. This means that the invention insures a cost reduction as well as numerous advantages in commercial processing.

EXAMPLE 1

A 30-gallon Pony ® mixer was charged with 23.94 kg of tapioca starch and 6 kg of dextrin J. P. and the charge was mixed for 10 minutes to give a tapioca starch-dextrin mixed powder.

Separately, 60 g of cyanocobalamin was dissolved in 4.5 l of pure water followed by addition of 4.5 l of ethanol.

This solution was added into the Pony ® mixer containing the tapioca starch-dextrin mixed powder and the mixture was kneaded for 20 minutes to give granules.

The granules were dried in vacuo at 40° C. to remove the water and ethanol.

The dry product was pulverized with an atomizer fitted with a 1 mm (dia.) screen to give a cyanocobalamin 500-fold powder (containing 0.2 weight %).

This diluted powder was a pink powder and its loss on drying was 6.6%.

EXAMPLE 2

A 75-liter super mixer was charged with 7.99 kg of tapioca starch followed by addition of 2 kg of dextrin J. P. and the mixture was stirred for 1 minute to give a tapioca starch-dextrin mixed powder.

Separately, 10 g of cyanocobalamin was dissolved in 1.5 l of pure water followed by addition of 1.5 l of ethanol.

This solution was added into the super mixer containing the above tapioca starch-dextrin mixed powder and the whole mixture was kneaded for 10 minutes to give granules.

The granules were dried in vacuo at 40° C. to remove the water and ethanol.

The resulting dry product was pulverized with an atomizer fitted with a 1 mm (dia.) screen to give a cyanocobalamin 1000-fold powder (0.1 weight %).

This diluted powder was a pink powder and its loss on drying was 4.5%.

EXAMPLE 3

A 75-liter super mixer was charged with 7.99 kg of corn starch followed by addition of 2 kg of dextrin J. P. and the mixture was stirred for one minute to give a corn starch-dextrin mixed powder.

Separately, 10 g of cyanocobalamin was dissolved in 1.5 l of pure water followed by addition of 1.5 l of ethanol.

This solution was added into the super mixer containing the above corn starch-dextrin mixed powder and the mixture was kneaded for 10 minutes to give granules.

The granules were dried in vacuo at 40° C. to remove the water and ethanol.

The resulting dry product was pulverized with an atomizer fitted with a 1 mm (dia.) screen to give a cyanocobalamin 1000-fold powder (0.1 weight %).

This diluted powder was a pink powder and its loss on drying was 5.6%.

EXAMPLE 4

A vertical granulator was charged with 790 g of corn starch and 200 g of dextrin J. P. to give a corn starch-dextrin mixed powder.

Separately, 10 g of cyanocobalamin was dissolved in 150 ml of pure water followed by addition of 150 ml of ethanol.

The above solution was added into the vertical granulator containing the corn starch-dextrin mixed powder and the mixture was kneaded to give granules.

The granules were dried in vacuo at 40° C. to remove the water and ethanol.

The resulting dry product was crushed in a power mill fitted with a 1 mm (dia.) screen to give a cyanocobalamin 100-fold powder (1.0 weight %).

The resulting diluted powder was a pink powder and its loss on drying was 5.5%.

EXAMPLE 5

A fluidized-bed granulator was charged with 890 g of corn starch and 50 g of dextrin J. P.

Separately, 10 g of cyanocobalamin and 50 g of dextrin were dissolved in 250 ml of pure water.

This solution was spray-dried in the fluidized-bed granulator containing the corn starch and dextrin to give granules.

The granules were crushed in a power mill fitted with a 1 mm (dia.) screen to give a cyanocobalamin 100-fold powder (1.0 weight %).

This diluted powder was a pink powder and its loss on drying was 7.1%.

Assay of vitamin $B_{12}$ compounds

Each vitamin $B_{12}$-containing sample was extracted with 0.1% phosphoric acid-methanol (3:1, v/v) and the extract was subjected to liquid chromatography.

A column packed with octadecyl-silica gel was used as the assay column and 0.05 mol ammonium dihydrogen phosphate-methanol (7:3, v/v) as the mobile phase. The determination was performed at the wavelength of 550 nm.

TEST EXAMPLE 1

Stability of vitamin $B_{12}$ diluted powder itself

Ten grams each of the diluted powders prepared in Examples 1 to 5 (the equivalent of 10 mg cyanocobalamin in the case of the 1000-fold powder, 100 mg in the case of the 100-fold powder, and 20 mg in the case of the 500-fold powder) was placed in a glass bottle and stored at 60° or 50° C./68% RH.

In the test at 60° C., the glass bottle was kept closed. In the test at 50° C. and 68% RH, the glass bottle was kept open.

The samples were taken out after 2 weeks of storage and the cyanocobalamin content, loss on drying, and change in appearance were determined. The results are set forth in Table 1.

As the control, a commercial vitamin $B_{12}$ 0.1% powder (Roche, vitamin $B_{12}$ 0.1% SD 5316, Roche Chemical Division) was used.

TABLE 1

| Storage conditions | 60° C., 2 weeks, closed | 50° C. & RH 68%, 2 weeks, closed |
| --- | --- | --- |
| Example 1 | 100.5 | 100.4 |
| Example 2 | 99.5 | 99.0 |
| Example 3 | 99.6 | 100.3 |
| Example 4 | 99.7 | 99.7 |
| Example 5 | 97.5 | 96.5 |
| Comparative Example | 94.1 | 94.9 |

Unit: % residue from initial

TEST EXAMPLE 2

Formulation stability with ascorbic acid

Fifty grams each of the diluted powders prepared in Examples 1 to 5 (the equivalent of 50 mg in the case of the 1000-fold powder, 500 mg in the case of the 100-fold powder, and 100 mg in the case of the 500-fold powder) was mixed with 100 g of ascorbic acid and 10 g of each mixture was stored in a glass bottle at 60° C.

This test was performed with the bottles closed.

The samples were taken out after 2 weeks of storage and the cyanocobalamin content, loss on drying, and change in appearance were determined. The results are set forth in Table 2.

As the control, a commercial vitamin $B_{12}$ 0.1% powder (Roche, vitamin $B_{12}$ 0.1% SD 5316, Roche Chemical Division) was used.

TABLE 2

| Storage conditions | 60° C., 2 weeks, closed |
| --- | --- |
| Example 1 | 100.6 |
| Example 2 | 100.1 |
| Example 3 | 99.8 |
| Example 4 | 95.9 |
| Example 5 | 94.2 |
| Comparative Example | 95.0 |

Unit: % residue from initial

TEST EXAMPLE 3

Formulation stability with vitamin $B_1$ and vitamin $B_6$

Fifty grams each of the diluted powders prepared in Examples 1 to 5 (the equivalent of 50 mg cyanocobalamin in the case of the 1000-fold powder, 500 mg in the case of the 100-fold powder, and 100 mg in the case of the 500-fold powder) was mixed with 130 g of thiamin nitrate and 10 g of pyridoxine hydrochloride and the mixture was placed in a glass bottle and stored at 60° C. or 50° C./68% RH.

In the test at 60° C., the glass bottle was kept closed. In the test at 50° C. and 68% RH, the glass bottle was kept open.

The samples were taken out after 2 weeks of storage and the cyanocobalamin content, loss on drying, and change in appearance were determined. The results are set forth in Table 3.

As the control, a commercial vitamin $B_{12}$ 0.1% powder (Roche, vitamin $B_{12}$ 0.1% SD 5316, Roche Chemical Division) was used.

TABLE 3

| Storage conditions | 60° C., 2 weeks, closed | 50° C. & RH 68%, 2 weeks, closed |
| --- | --- | --- |
| Example 1 | 96.2 | 89.9 |
| Example 2 | 97.2 | 94.2 |
| Example 3 | 97.0 | 93.0 |
| Example 4 | 96.7 | 94.3 |
| Example 5 | 95.9 | 83.0 |
| Comparative Example | 96.5 | 74.6 |

Unit: % residue from initial

We claim:

1. A vitamin $B_{12}$ composition produced by mixing water-insoluble granular starch with dextrin to form an adsorbent carrier, uniformly kneading said adsorbent carrier with an added aqueous solution of vitamin $B_{12}$ which solution comprises an aqueous solvent in a proportion of 250 to 0.7% (V/W) relative to the total amount of vitamin $B_{12}$, water-insoluble granular starch and dextrin and subsequently drying the resultant mixture, the amount of vitamin $B_{12}$ in the composition being 0.05 to 1.0 weight percent based on the total amount of vitamin $B_{12}$, granular starch and dextrin and the amount of dextrin in the composition being 5 to 30 weight percent based on the total amount of vitamin $B_{12}$, granular starch and dextrin.

2. A composition according to claim 1 wherein the vitamin $B_{12}$ is cyanocobalamin.

* * * * *